United States Patent [19]

Eguchi

[11] 4,066,793

[45] Jan. 3, 1978

[54] SEASONING COMPOSITION AND PREPARATION THEREOF

[75] Inventor: Hajime Eguchi, Yokohama, Japan

[73] Assignee: Ajinomoto Co., Inc., Tokyo, Japan

[21] Appl. No.: 690,365

[22] Filed: May 26, 1976

Related U.S. Application Data

[63] Continuation-in-part of Ser. No. 557,787, March 12, 1975, abandoned.

[30] Foreign Application Priority Data

Mar. 18, 1974 Japan .................................. 49-30764

[51] Int. Cl.$^2$ ...................... A23L 1/229; A23L 1/23; A23L 1/28
[52] U.S. Cl. ..................................... 426/60; 426/533; 426/650
[58] Field of Search .................. 426/60, 62, 534, 650, 426/656, 533

[56] References Cited

U.S. PATENT DOCUMENTS

| | | |
|---|---|---|
| 2,928,740 | 3/1960 | Rosenthal et al. ...................... 426/62 |
| 2,946,688 | 7/1960 | Rosenthal et al. ...................... 426/62 |
| 3,627,539 | 12/1971 | Ishii et al. ........................... 426/62 X |
| 3,711,301 | 1/1973 | Asogawa et al. ................. 426/650 X |
| 3,778,513 | 12/1973 | Shiga et al. ....................... 426/650 X |

Primary Examiner—Raymond N. Jones
Assistant Examiner—Esther M. Kepplinger
Attorney, Agent, or Firm—Cooper, Dunham, Clark, Griffin & Moran

[57] ABSTRACT

Seasoning compositions, and processes for their production, which have an improved and enhanced meat-like flavor, and comprise mixtures containing extracts of yeast autolysates, 5'-nucleotides, sodium chloride and potassium salts; the potassium ion concentration being more than 0.5 times the sodium ion concentration.

28 Claims, No Drawings

SEASONING COMPOSITION AND PREPARATION THEREOF

RELATED APPLICATION

This application is a continuation-in-part of copending application Ser. No. 557,787 filed Mar. 12, 1975 now abandoned.

This invention relates to the preparation of seasoning materials containing yeast extract as a main component. More particularly, it is concerned with the preparation of seasoning compositions having improved and enhanced meatlike flavor comprising a mixture of extract of yeast autolysate, 5'-nucleotides, NaCl, and potassium salts, and the seasoning composition prepared thereby.

An object of the present invention is to provide an improved seasoning composition based on yeast extract and a process for preparing the same by which improved meat-like flavor may be imparted to foods.

Recently there has been a demand for seasonings capable of imparting a so-called thickness or body to foods. These include, for example, beef and whale extracts. This demand has constantly increased throughout the world, and it is expected that such demand will increase significantly in the future. However, as the supply of beef extracts or whale extracts is limited and as suitable seasonings are currently in short supply, the aforesaid demand constitutes a very important problem, especially for the makers of processed foods.

Yeast extracts prepared from bakers yeast, Japanese sake yeast and beer yeast which are easily obtainable in large quantities at low price have been used as components of seasonings. However, these extracts have unfavorable odors peculiar to yeast and are lacking in the thickness and body which can be obtained with meat extracts, and they are inferior to the meat extracts in their taste quality.

Yeast extracts can be prepared by autolysis or by hydrolysis using enzymes, acid or alkali.

Among these three methods, extracts prepared by autolysis seem to be relatively good quality; however, the problems mentioned above still remain. Accordingly, the use of yeast extracts in the field of processed food manufacturing has been limited to a partial replacement of beef extract, and it has been thought up to now that the quality of yeast extract is not good enough to permit independent use for seasoning.

It is, therefore, a principal object of the instant invention to provide new types of seasoning compositions containing yeast extracts as a main component, and having improved qualities which make them independently useful for food processing.

It has been discovered that the quality of yeast extracts are generally greatly affected by the balance of inorganic ions, particularly cations, included in the final yeast extracts produced, and also that an interaction between said inorganic ions and 5'-nucleotides is quite important for attaining the thickness and body which has been observed in beef or meat extracts.

The high quality seasonings prepared by the present process are characterized as having less of the unfavorable, strange odors peculiar to yeast itself, and by having a thickness or body in taste which resembles that of beef extract or shin extract prepared by concentrating extract of boiled shin. These characteristics are apparent from tasting a soup containing 2% of yeast extract and 0.5-0.8% NaCl at 60°-70° C.

Characteristic features of the present invention are as follows:
1. The seasonings comprise mixtures containing yeast extracts, potassium salts, sodium chloride and 5'-nucleotides in which the potassium ion concentration is more than 0.5 times that of sodium ions.
2. The presently preferred process for preparing the seasonings comprises the steps of:
    1. decomposing suspended yeast cells by autolysis in the presence of potassium ions at a pH of 5 to 7 and a temperature of from 30° to 60° C, and thereafter performing the following steps in any convenient order;
    2. adding from 5 to 20% by weight sodium chloride, so that the [K+]/[Na+] ratio is more than 0.5,
    3. separating resulting clear extract from the insoluble residue,
    4. heating at from 90° C to 100° C for from 10 to 30 minutes, and
    5. adding from 0.5 to 4% by weight of a 5'-nucleotide.

The favorable taste of the present seasoning compositions is substantially realized by a mutual interaction between 5'-nucleotide, inorganic ions and amino acids from the yeast extract. It is also very important to control a balance of inorganic ions and 5'-nucleotide.

While the precise quantative balance between sodium ions and potassium ions cannot be exactly determined, it presently appears desirable that the amount of potassium ions which may be provided as inorganic or organic compounds is larger than 0.5 times, and preferably between 1 and 5 times, the amount of sodium ions in the final seasoning compositions. The inorganic or organic compounds which provide potassium ions are preferably added at an early stage in the hydrolysis.

The inorganic or organic compounds which provide potassium ions include, for example, inorganic salts such as potassium dihydrogen phosphate, dipotassium hydrogen phosphate, potassium chloride and potassium carbonate, organic salts such as potassium bitartrate, potassium glutamate, potassium aspartate, potassium lactate, potassium succinate, potassium citrate, potassium malate, potassium fumarate and potassium gluconate.

For autolysis, the quantity of yeast cells in the suspension is preferably 5 to 30% by weight relative to the weight on a dry basis. The autolysis is usually performed at a pH value between 5.0 to 7.0, and at a temperature between 30° and 60° C, and more preferably pH 6.0–6.5 at 45°–55° C. It is usually carried out for 10 to 50 hours. The optimum temperature depends upon other conditions mentioned above. It may also be useful for effective autolysis to add a stimulator of autolysis such as ethyl acetate.

Any of a variety of edible yeasts may be employed. These include bakers yeast such as *Saccharomyces cerevisiae* CBS 1172 and CBS 1234, beer yeast such as *Saccharomyces cerevisiae* CBS 1171, CBS 1230 and *Saccharomyces uvarum* CBS 1503, and *Saccharomyces carlsbergensis* IFO 2015, sake yeast such as *Saccharomyces cerevisiae* IFO 2165, IFO 2342 and *Candida sake* CBS 159, wine yeast such as *Saccharomyces cerevisiae* IAM 4274, Awamori yeast such as *Saccharomyces awamori* IBL 2788 yeasts employed for preparation of miso (fermented soybean paste) or soy sauce such as *Saccharomyces rouxii* CBS 4632, CBS 4634 and CBS 4022, *Pichia farinosa* CBS 2006 and CBS 2004 and yeasts employed for ripening of cheese such as *Saccharomyces cerevisiae* CBS 438 and *Kluyveromyces lactis* ATCC 20185.

The process is not limited to the specific strains mentioned above. Useful, edible yeast strains of the genera Saccharomyces, Candida, Pichia and the like are readily available on the market or from culture collections.

The yeast strains identified in this specification by accession numbers preceded by CBS are freely available from the Centraalburear voor Schimmelkultures, Baarn, Netherlands. Those identified by accession numbers preceded by IFO are available from the Institute for Fermentation, Osaka, Japan, and those identified by accession numbers preceded by ATCC are available from the American Type Culture Collection in Rockville, Md. U.S.A.

For use in the invention, yeast cells are prepared by entirely conventional methods using a medium containing carbohydrates such as glucose, fructose, maltose, sucrose, starch, starch hydrolyzate, and molasses, organic acids such as acetic acid, propionic acid, fumaric acid, and alcohols such as methanol and ethanol as a carbon source. Yeast cells obtained as residues from the brewing of beer, sake and wine are especially useful in the practice of the invention. They may be used for autolysis without the actual isolation of the cells.

The insoluble residue included in the autolysate solution prepared in the above mentioned first process is removed at any convenient time by conventional methods such as centrifugation, ordinary filtration and ultrafiltration. The extract is heated in order to inactivate those enzymes in the solution which catalyze autolysis and decomposition of 5'-nucleotides. The heat treatment is preferably at 90° C to 100° C for from 10 to 30 minutes.

As indicated above, Steps 2 through 5 can be carried out in any convenient order. Naturally, the 5'-nucleotides should not be kept in the presence of nucleotidases from the yeast autolysates for too extensive a period of time while the mix is at a temperature at which the enzymes are active. It is therefore preferred to heat the mix before the 5'-nucleotides are added so as to inactivate the enzymes. It is not necessary to do so, however, since the mix can be cooled to inactivate the enzymes before addition of the 5'-nucleotides. Alternatively, the mix can be heated shortly after the addition of the 5'-nucleotides.

As a result of interaction between a 5'-nucleotide, potassium ions and sodium ions, the seasoning composition of the present invention is given a well balanced and thick flavor, and a beef or shin extract-like flavor can be realized. These effects in flavor are greatly reduced if a compound containing potassium ions was not added in said first process.

Typical 5'-nucleotides which may be employed include 5'-inosinic acid, 5'-guanilic acid, their physiologically acceptable salts such as alkali metal salts and alkaline earth metal salts, and mixtures thereof. The amount of 5'-nucleotide added is normally from 0.5 to 4% based on the weight of the final seasoning composition. It has been found that the flavor enhancing or improving effects of 5'-nucleotides tend to increase with increasing ratio of potassium ions to sodium ions.

The addition of NaCl is important to improve the balance of flavor and its preservability. It is best that it be added after autolysis but before removal of the insoluble substance, because this simplifies the removal process. The amount of NaCl added is normally from 5 to 20% based on the weight of the final seasoning composition.

The seasoning compositions of the present invention may contain other known seasoning ingredients such as monosodium glutamate, methionine, glycine, alanine, lysine and the like. Those ingredients may be added at any time during the above mentioned processes.

The seasoning compositions obtained may be added as solutions to foods and beverages. They may also be employed as pastes with a water content of 30 to 55%, or in the form of powders or granules prepared by conventional method such as spray-drying.

The following non-limiting examples are given by way of illustration only.

EXAMPLE 1

Bakers yeast (*Saccharomyces cerevisiae* CBS 1172) was cultured at 30° C with aerobic shaking in a medium containing 3% cane molasses calculated as sugar, 0.1% $KH_2PO_4$, 0.1% corn steep liquor, 0.5% $(NH_4)_2SO_4$ and 0.05% $MgSO_4.7H_2O$. After 24 hours cultivation, yeast cells were harvested by centrifugation and washed with water to obtain yeast cells in a creamy state (yeast cream) with a water content of 42%.

Water was added to 2.24 kg of the yeast cream to prepare 10 kg water suspension of yeast cells. Into the suspension, 49.5 g $KH_2PO_4$, 169 g $K_2HPO_4$ and 218.4 g d-potassium bitartrate was dissolved completely and thereafter its pH value was adjusted to 6.5.

The suspension was mixed with 50 ml ethyl acetate and mixed well by shaking, and allowed to stand for 20 hours at 52° C for autolysis of the yeast cells. The solution after being autolyzed was adjusted to pH 5.5 with hydrochloric acid, and 1 kg NaCl was dissolved in the solution. From the solution treated as mentioned above, clear soluble fraction was obtained by centrifugation. The solution used to wash the residue was added to the clear solution.

After being heated at 98° C for 30 minutes, 2% of 5'-sodium inosinate was added to the clear solution. Then by concentrating the fraction under reduced pressure, 2.72 kg of modified yeast extract of which water concentration is 50% were obtained (sample A).

Potassium ions concentration ([K+]) and sodium ions concentration ([Na+]) were determined by conventional method, and were found to be 5.7% and 4.2% respectively. Therefore, [K+]/[Na+] was 1.36.

The same kinds of modified yeast extracts, samples B, C, D and E were similarly prepared except for variations in the amount of $KH_2PO_4$, $K_2HPO_4$ and d-potassium bitartrate. The amounts used were such that the ratio, [K+]/[Na+], was 0.34 for sample B, 0.50 for sample C, 0.75 for sample D and 2.00 for sample E.

Sample F contained no potassium salts.

The yield of modified yeast extracts based on the yeast cells employed in samples A-F were all about 50% relative to the weight on a dry basis.

As a control, shin extract was prepared by the following process: 5.5 kg shin which were cut to about 2 cm cubes were added to 18 liters of water and boiled down to one third of the original volume with a low fire during which process the lye and oily materials rising to the surface were removed.

The extract prepared was concentrated under reduced pressure to obtain 500 g of shin extract with a water content of 50%.

The samples A-F were subjected to organoleptic testing by a panel of 20 members who had been specially trained for this kind of test.

The panel test was performed by the following procedure: solutions of sodium chloride of 0.6% conc. were added to samples A-F and to the shin extract which was used as a control in an amount of 2% conc. respectively, and panel members were asked to give marks about degree of thickness and body of each sample solution in contrast to those of shin extract marked as 10.

The average marks were 9.2 for the samples A and E, 9.0 for the sample D, 8.5 for the sample C, 6.0 for the sample B whose [K+]/[Na+] ratio was under 0.5, and 5.0 for the sample F to which potassium salt was not added at all. This result apparently shows the importance of maintaining a [K+]/[Na+] ratio of more than 0.5.

The panel was also asked to comment on the degree of unfavorable strange odors peculiar to yeast in each sample solution prepared as mentioned above. The strange odors in samples A-E were all weaker than that of Sample F to which potassium salt was not added at all, and it was found that the strange odor decreased with increasing [K+]/[Na+] ratio.

All panel members indicated that samples A-E had more favorable taste than sample F, and that the favorable taste increased with increasing [K+]/[Na+] ratio.

EXAMPLE 2

Modified yeast extract (Sample G) was prepared in the same manner as described in Example 1 for preparing sample A but without addition of 5'-inosinic acid.

Three kinds of test solution were prepared by adding 2% of sample A, sample G and shin extract prepared as mentioned in Example 1 respectively into 0.6% conc. sodium chloride solution. The three test solutions were offered for organoleptic test by a panel of 20 members, as described above.

The average mark of sample A was 9.2, and of sample G, 6.0. These results show that addition of 5'-inosinic acid to the modified yeast extract is important for attaining a thickness and body peculiar to shin extract.

EXAMPLE 3

Water suspension of bakers yeast cells was prepared as in Example 1.

Autolysis of the bakers yeast cells in suspension with ethyl acetate was carried out at pH 6.5, at 52° C for 6 hours, and then the solution was supplemented with potassium salts in the same manner as described in Exampkle 1 as a process for preparation of sample A. Thereafter, said autolysis was carried out for a further 14 hours under the same conditions. The solution prepared was treated in the same manner as described in Example 1 to prepare sample H.

Sample I was also prepared in the same manner as described in Example 1 for the preparation of sample A but the potassium salts were added after 20 hours' autolysis.

Four kinds of test solutions for organoleptic test were prepared by adding 2% of sample A, sample H, sample I and shin extract prepared as in Example 1 to 0.6% conc. sodium chloride solutions.

The test by 20 panel members were performed as described above.

The average mark of the sample was 9.2, but those of sample H and I were 7.0 and 6.5 respectively. All test panel members pointed out that the strange odor of sample A was the weakest and that of sample I was the strongest.

When said panel members were asked about degree of favorable taste of each sample solution, all members indicated that there was no significant difference between those three samples A, H and I.

EXAMPLE 4

Beer yeast (*Saccharomyces cerevisiae* CBS 1171), sake yeast (*Saccharomyces cerevisiae* IFO 2165), wine yeast (*Saccharomyces awamori* IBL 2788), miso or soy sauce yeast (*Saccharomyces rouxii* CBS 4632) and yeast for ripening of cheese (*Saccharomyces cerevisiae* CBS 438) were cultured under conventional conditions in a culture medium having the same composition as Example 1. Cultivation was terminated when each yeast reached its maximum growth, and the yeast cells were harvested by centrifugation and washed with water. As a result, yeast creams containing 42% water were obtained.

Water suspensions of respective yeast cells containing 15% by weight of the yeast cells calculated as dry matter were prepared by using 1 kg of each yeast cream.

To the water suspensions were added 3.8% $KH_2PO_4$ and 13% $K_2HPO_4$ relative to the weight of dry cells, and 7% of 50% conc. lactic acid which was neutralized with $K_2CO_3$. These suspensions, in which the above mentioned compounds were dissolved completely, were then adjusted to pH 6.5.

To each suspension, 0.5% ethyl acetate was added and mixed well by shaking, and they were allowed to stand for 24 hours at 50° C for autolysis of the yeast cells. The treated suspensions after being autolyzed were adjusted to pH 5.5 with hydrochloric acid, and thereafter NaCl was dissolved into them in an amount of 10% relative to the final volume. Clear soluble fractions were obtained from each solution by centrifuging.

After being heated at 98° C for 30 minutes, each of the soluble fractions was mixed with 2% of 5'-sodium inosinate relative to the final volume, and concentrated under reduced pressure until its water concentration was about 50%.

Solutions for organoleptic test were prepared by adding 2% of the modified yeast extracts prepared as mentioned above, the sample A prepared in Example 1, and shin extract prepared in Example 1 respectively into 0.6% conc. sodium chloride solution. These solutions were offered for the panel test by a panel of 20 members, and the panel test was performed by requesting evaluation of their flavor in contrast to the shin extract. All panel members indicated that all samples had a favorable thickness and body similar to shin extract, although there were some differences in yeast-like odor between the samples.

EXAMPLE 5

*Pichia farinosa* CBS 2006 was inoculated into a medium containing 0.5% ammonium acetate, 0.2% $KH_2PO_4$, 1% corn steep liquor, 0.5% $(NH_4)_2SO_4$, 0.1% $MgSO_4.7H_2O$, and cultivation was carried out after adding a mixture of acetic acid and ammonium acetate to adjust the pH to 6.0. The cultivation was stopped when maximum growth was attained, and yeast cells were harvested by centrifugation. After washing with water, yeast cream with a water content of 45% was obtained.

A modified yeast extract was prepared by using yeast cream obtained in the same manner described in Example 4.

As a result of organoleptic test performed in the same manner described in Example 4, all panel members indicated that this extract had a favorable flavor in thickness and body which was similar to that of shin extract.

EXAMPLE 6

An autolyzed cell suspension adjusted to a pH of 5.5 was prepared in the same manner described as in Example 1. The clear soluble fraction was obtained by centrifugation. The residue was washed with water and the washings were added to the clear fraction, then 1.0 kg of sodium chloride was dissolved in the clear fraction and sample G was prepared from the fraction in the same manner described as in Example 1.

Sample H was prepared by following the abovementioned procedure to prepare sample G except that the sodium chloride was added after heating.

Sample I was prepared by the following method:

A third clear soluble fraction which had been prepared in the same manner described as in Example 1 was cooled to 10° C, and 2% of 5'-sodium inosinate was added while maintaining the same temperature for 60 minutes. The solution was thereafter heated to, and maintained at 98° C for 30 minutes and sample I was prepared from the solution.

Three test solutions were separately prepared by adding 2% of samples G, H and I respectively into 0.6% conc. sodium chloride solution. Shin extract prepared in the same manner as in Example 1 was used as control. These solutions were tested by a panel of 20 members. The average mark of sample I was 9.0 and those of the remaining samples were all 9.2 in contrast to the shin extract marked as 10.

All the panel members indicated that there was no significant difference among these samples with respect to favorable taste and characteristic yeast-like odor.

What is claimed is:

1. A process for the preparation of a seasoning composition which comprises:
   1. decomposing suspended yeast cells by autolysis in the presence of potassium ions at a pH of 5 to 7 at a temperature of 30° C to 60° C, and thereafter performing the following steps in any selected order:
   2. adding from 5% to 20% by weight sodium chloride so that the [K+]/[Na+] ratio is more than 0.5,
   3. separating clear extract from the insoluble residue,
   4. heating at from 90° C to 100° C for from 10 to 30 minutes, and
   5. adding from 0.5% to 4% of a 5'-nucleotide;
   the percent by weight being based on the weight of the final composition.

2. A process as in claim 1 wherein Step 1 is followed by Steps 2, 3, 4 and 5.
3. A process as in claim 1 wherein Step 1 is followed by Steps 2, 3, 5, and 4.
4. A process as in claim 1 wherein Step 1 is followed by Steps 2, 4, 3 and 5.
5. A process as in claim 1 wherein Step 1 is followed by Steps 2, 4, 5 and 3.
6. A process as in claim 1 wherein Step 1 is followed by Steps 2, 5, 4 and 3.
7. A process as in claim 1 wherein Step 1 is followed by Steps 2, 5, 3 and 4.
8. A process as in claim 1 wherein Step 1 is followed by Steps 3, 2, 4, and 5.
9. A process as in claim wherein Step 1 is followed by Steps 3, 2, 5, and 4.
10. A process as in claim 1 wherein Step 1 is followed by Steps 3, 4, 2, and 5.
11. A process as in claim 1 wherein Step 1 is followed by Steps 3, 4, 5, and 2.
12. A process as in claim 1 wherein Step 1 is followed by Steps 3, 5, 2, and 4.
13. A process as in claim 1 wherein Step 1 is followed by Steps 3, 5, 4, and 2.
14. A process as in claim 1 wherein Step 1 is followed by Steps 4, 2, 3, and 5.
15. A process as in claim 1 wherein Step 1 is followed by Steps 4, 2, 5, and 3.
16. A process as in claim 1 wherein Step 1 is followed by Steps 4, 3, 2, and 5.
17. A process as in claim 1 wherein Step 1 is followed by Steps 4, 3, 5, and 2.
18. A process as in claim 1 wherein Step 1 is followed by Steps 4, 5, 2, and 3.
19. A process as in claim 1 wherein Step 1 is followed by Steps 4, 5, 3, and 2.
20. A process as in claim 1 wherein Step 1 is followed by Steps 5, 2, 3, and 4.
21. A process as in claim 1 wherein Step 1 is followed by Steps 5, 3, 2, and 4.
22. A process as in claim 1 wherein Step 1 is followed by Steps 5, 4, 3, and 2.
23. A process as in claim 1 wherein Step 1 is followed by Steps 5, 2, 4, and 3.
24. A process as in claim 1 wherein Step 1 is followed by Steps 5, 3, 4, and 2.
25. A process as in claim 1 wherein Step 1 is followed by Steps 5, 2, 3, and 4.
26. A process as in claim 1, wherein said yeast cells are prepared by conventional cultivation of a yeast strain selected from the group of genera consisting of Saccharomyces, Candida and Pichia.
27. A process as in claim 1 wherein said potassium salts are edible inorganic or organic potassium salts selected from the group consisting of potassium dihydrogen phosphate, dipotassium hydrogen phosphate, potassium chloride, potassium carbonate, potassium bitartrate, potassium glutamate, potassium asparate, potassium citrate, potassium malate, potassium fumarate and potassium gluconate.
28. A product prepared by the process of claim 1.